United States Patent [19]

Morris

[11] Patent Number: 4,493,890
[45] Date of Patent: Jan. 15, 1985

[54] ACTIVATED APOGLUCOSE OXIDASE AND ITS USE IN SPECIFIC BINDING ASSAYS

[75] Inventor: David L. Morris, Elkhart, Ind.

[73] Assignee: Miles Laboratories, Inc., Elkhart, Ind.

[21] Appl. No.: 404,427

[22] Filed: Aug. 2, 1982

Related U.S. Application Data

[63] Continuation-in-part of Ser. No. 246,591, Mar. 23, 1981, abandoned.

[51] Int. Cl.$^3$ .................. G01N 33/54; C12N 9/96
[52] U.S. Cl. .................................. 435/7; 435/188; 435/810; 436/547
[58] Field of Search .................. 435/7, 188, 184, 190, 435/25, 810; 424/85; 436/512, 536, 537, 543, 544, 547

[56] References Cited

U.S. PATENT DOCUMENTS 4,281,061  7/1981  Zuk et al. .............................. 435/7
4,318,982  3/1982  Hornby et al. ....................... 435/7

OTHER PUBLICATIONS

Rose et al., *Principles of Immunology*, MacMillan Publishing Co., N.Y., (1979), pp. 49–52.
Green et al., J. Immun., vol. 104, pp. 1094–1100, (1970).

*Primary Examiner*—Blondel Hazel
*Attorney, Agent, or Firm*—Andrew L. Klawitter

[57] ABSTRACT

A method for increasing the ability of apoglucose oxidase to combine with flavin adenine dinucleotide (FAD) and derivatives thereof to form active glucose oxidase by interacting apoglucose oxidase with an immunologically derived binding substance, e.g., an antibody or a fragment thereof, having a specific binding affinity for glucose oxidase. The apoglucose oxidase/anti-glucose oxidase immune complex is characterized by enhanced ability to combine with FAD and FAD-derivatives to yield glucose oxidase activity. The activation is particularly significant at temperatures elevated from room temperature, e.g., between 30°–45° C. An improved homogeneous specific binding assay method is provided for determining ligands wherein an FAD label is used and is monitored by its ability to combine with apoglucose oxidase to form active glucose oxidase by including anti-glucose oxidase in the reaction mixture.

33 Claims, 2 Drawing Figures

ACTIVATED APOGLUCOSE OXIDASE AND ITS USE IN SPECIFIC BINDING ASSAYS

CROSS-REFERENCE TO RELATED APPLICATIONS

This is a continuation-in-part of application Ser. No. 246,591, filed Mar. 23, 1981 now abandoned.

BACKGROUND OF THE INVENTION

1. Field of the Invention

This invention relates to a method for increasing the ability of apoglucose oxidase to combine with flavin adenine dinucleotide (FAD) and FAD derivatives to form active glucose oxidase, i.e., a method for activating apoglucose oxidase. The invention further relates to homogeneous specific binding assay methods, reagent means, and test kits for determining a ligand, such as an antigen, hapten or antibody, in a liquid medium wherein FAD is employed as label and wherein the FAD label is monitored by its ability to combine with apoglucose oxidase to form active glucose oxidase.

Glucose oxidase is a conjugated enzyme composed of an enzymatically inactive, high molecular weight protein component (apoenzyme) and FAD (a low molecular weight, nonproteinaceous prosthetic group). Apoglucose oxidase and FAD have a high binding affinity (binding constant of around $10^{10}$ molar$^{-1}$), but can be effectively separated by treatment with acidified ammonium sulfate [Swoboda, Biochim. Biophys. Acta 175: 365-379(1969)]. Swoboda demonstrated that apoglucose oxidase exists in solution mainly with the molecular configuration of a loose flexible coil, and to a lesser extent in a compact globular form, whereas when FAD is added the protein is converted to a compact, nearly spherical form having glucose oxidase activity. FAD is understood to most efficiently bind with the globular form of apoglucose oxidase to yield active glucose oxidase. Stabilization of apoglucose oxidase by intramolecular crosslinking with glutaraldehyde has been reported [Solomon et al, Biopolymers 16: 1837-1952(1977)]. As used herein, apoglucose oxidase shall be understood to include any protein preparation having apoglucose oxidase activity, i.e., having the ability to generate glucose oxidase activity upon addition of FAD, thus including unmodified apoglucose oxidase obtained by dissociation of glucose oxidase or a chemically modified form thereof.

2. Brief Description of the Prior Art

U.S. Pat. No. 4,238,565 assigned to the present assignee describes specific binding assay methods wherein FAD is employed as label and is monitored by its ability to combine with apoglucose oxidase to form active glucose oxidase. Both homogeneous and heterogeneous formats are anticipated. In a homogeneous assay for determining an antigen in a liquid medium, a test sample of the liquid medium is combined with antibody to the antigen and with a labeled conjugate comprising the antigen or an analog thereof coupled to FAD whereby any antigen from the sample competes with antigen-FAD for binding with antibody. Apoglucose oxidase is also present or is added after an appropriate incubation period and is capable of combining with antigen-FAD which has not been bound by antibody to yield active glucose oxidase. However, antibody-bound antigen-FAD is not capable of such combination with apoglucose oxidase. Consequently, the concentration of antigen in the test sample dictates the amount of measurable glucose oxidase which results. Glucose oxidase activity is measurable in a wide variety of known manners, including colorimetric methods.

The FAD-labeled homogeneous specific binding assay is generally applicable to the determination of a wide variety of ligands over a wide range of concentrations. However, application of the assay method to certain existing analytical instrumentation requiring incubation of the assay reaction mixture at elevated temperatures and for short periods has been found to be limited. It has been found that the ability of FAD and FAD-derivatives (i.e., ligand-FAD conjugates) to combine with apoglucose oxidase to form active glucose oxidase decreases rapidly with increasing temperature above room temperature, to the point that at temperatures above about 30° C. significantly greater amounts of apoglucose oxidase must be added to the assay reaction mixture to obtain a dose-response curve. At 35°-40° C., the FAD-apoglucose oxidase recombination reaction is slowed to the point that analytically useful dose-response curves are not possible to obtain with short incubation periods (e.g., 10 minutes or less) for the determination of ligands at concentrations below $10^{-6}$M.

The preparation of antibody to glucose oxidase is reported by Green et al, J. Immunol. 104: 1094-1100(1970). Apoglucose oxidase preparations useful in the FAD-labeled specific binding assay method are described in U.S. Pat. No. 4,268,631 assigned to the present assignee.

SUMMARY OF THE INVENTION

It has now been found that the ability of apoglucose oxidase to combine with FAD to form active glucose oxidase is increased by interacting apoglucose oxidase with an immunologically derived binding substance having a specific binding affinity for glucose oxidase. Such binding substance (hereinafter referred to as "anti-glucose oxidase") may be an antibody raised against glucose oxidase or a fragment thereof, e.g., Fab, F(ab'), or F(ab')$_2$, or any other substance having a specific binding affinity for glucose oxidase, such as an aggregate, polymer, conjugate or crosslinked form of an antibody or antibody fragment. The apoglucose oxidase/anti-glucose oxidase complex has been found to be activated to recombination with FAD. The apoglucose oxidase activation has been found to increase with increasing temperatures between 25°-37° C. to the extent that at 37° C. the formation of active glucose oxidase is enhanced as much as 100 to 1000-fold by the presence of antiglucose oxidase. Thus, FAD-labeled homogeneous specific binding assays for ligands appearing in concentrations between $10^{-5}$ and $10^{-8}$M are made feasible for use with analytical instrumentation requiring elevated reaction temperatures (e.g., 37° C.) and short incubation periods (e.g., 5-7 minutes).

DESCRIPTION OF THE PREFERRED EMBODIMENTS

Figure 1:
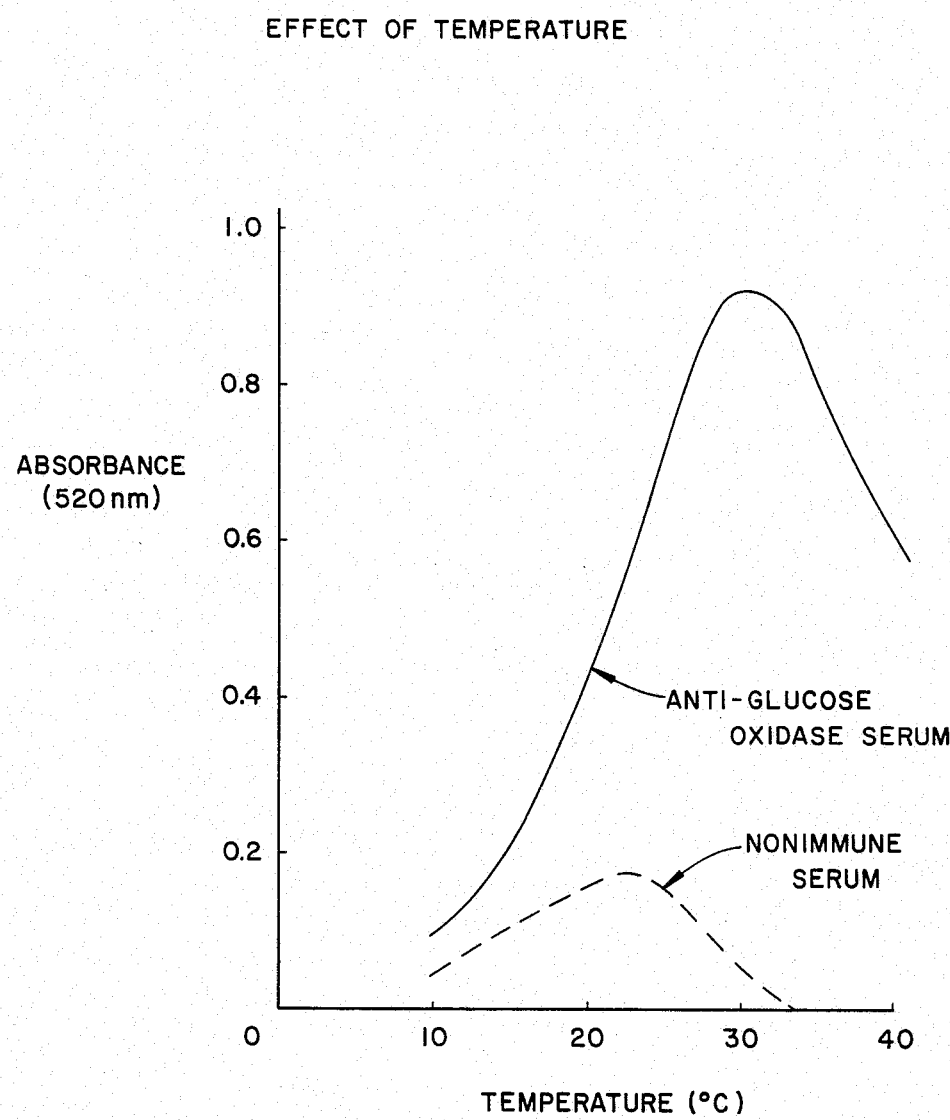
FIG. 1 is a graphical representation of data from the examples set forth below showing the effect of temperature on the apoglucose oxidase recombination reaction in the presence and absence of antiglucose oxidase.

In the context of this disclosure, the following terms shall be defined as follows unless otherwise indicated:

Ligand—the analyte which is the object of an assay, i.e., the substance, or class of related substances, whose presence or amount in a liquid medium is under determination.

Specific binding partner of the ligand—any substance, or class of substances, which has a specific binding affinity for the ligand to the exclusion of other substances.

FAD-labeled specific binding assay—an assay, usually an immunoassay, of any of the homogeneous types described in the aforesaid U.S. Pat. No. 4,238,565 incorporated herein by reference wherein the label is FAD.

Reagent means—a composition, test device or test kit comprising the reagents used to perform an FAD-labeled specific binding assay.

As used herein, apoglucose oxidase shall be understood to include any protein preparation having apoglucose oxidase activity, i.e., having the ability to generate glucose oxidase activity upon addition of FAD, thus including unmodified apoglucose oxidase obtained by dissociation of glucose oxidase or a chemically modified form thereof. Appropriate chemically modified forms of apoglucose oxidase include polymerized, aggregated, conjugated, and crosslinked forms. Crosslinking is a known method for stabilizing apoglucose oxidase (Solomon et al, supra) and can be accomplished by any conventional means, e.g., glutaraldehyde, diisocyanates, bis-imidates, bis-epoxides, and bis-activated esters (N-succinimidyl esters). In essence any chemical modification of the apoglucose oxidase preparation in the way of a protein modification made by one skilled in the protein chemistry art may be performed for purposes of stability or other reasons provided apoglucose oxidase activity is retained to a useable degree.

The anti-glucose oxidase of the present invention may be an antibody, an antibody fragment, or any other substance having a specific binding affinity for glucose oxidase and which is derived from immunological processes. When in the form of whole antibody, anti-glucose oxidase may be of any of the known classes, e.g., IgG, IgM, and so forth, and of any subclasses thereof. Any fragment of any such antibody which retains the specific binding affinity for glucose oxidase may also be employed, for instance, the fragments of IgG conventionally known as Fab, F(ab'), and F(ab')$_2$. In addition, aggregates, polymers, conjugates, and chemically modified, e.g., crosslinked, forms of the immunoglobulins or their fragments can be used where appropriate and desirable. Poly(anti-glucose oxidase), that is, a complex compound comprising more than one antibody or fragment, can be prepared in any available manner so as to maintain binding affinity for apoglucose oxidase. For instance, antibodies or antibody fragments can be aggregated or polymerized through the use of conventional protein-protein coupling and crosslinking reactions and reagents. Alternatively, antibodies or antibody fragments can be linked to synthetic or naturally occurring polymer backbones, such as protein or polysaccharide types, in conventional manners. Likewise, antibodies or fragments thereof can be chemically modified without destroying their anti-glucose oxidase activity such as by intermolecular crosslinking or modification of functional groups for purposes of affecting charge distributions, water or other solvent solubility, temperature stability, and the like as will be known by one working in the field of protein chemistry.

Immunoglobulin antibodies to glucose oxidase may be obtained by any known means. In particular, such antibodies may be obtained in the form of antiserum from an animal (e.g., mouse, rabbit, guinea pig, goat, etc.) which has been immunized against glucose oxidase or an immunogenic analog or derivative of glucose oxidase. The immunogen injected into the host animal will usually comprise a protein preparation having glucose oxidase activity, such protein preparation comprising unmodified protein obtained from an appropriate enzyme source, e.g., molds and microbes, or chemically modified protein, e.g., polymerized, aggregated, conjugated, or crosslinked protein. Methods for accomplishing desired chemical modifications will be available to one skilled in the art of protein chemistry. Antiglucose oxidase antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al, Springer-Verlag (New York 1978), Nature 266:495(1977), and Science 208:692 (1980).

The resulting anti-glucose oxidase preparation can be used in its undiluted form or in an appropriate diluted form to activate apoglucose oxidase, or can be purified by conventional means and the purified preparation then used in undiluted or diluted form. Conventional purification techniques involving protein precipitations, extractions, and chromatography, including affinity chromatography and related column chromatography techniques, can be applied. Additionally or alternatively, anti-glucose oxidase which has an affinity for binding denatured or inactive apoglucose oxidase can be removed if desired by adsorbing such material out of the preparation by contact with denatured or inactive apoenzyme and optionally removing resulting anti-glucose oxidase bound to the denatured or inactive apoenzyme. Activation of apoglucose oxidase by anti-glucose oxidase is believed to result from the formation of an immune complex which tends to hold the apoenzyme in a molecular configuration favoring the formation of active glucose oxidase upon binding with FAD.

The amount of anti-glucose oxidase to be added to a given amount of apoglucose oxidase to give optimum activation will be determined empirically. It has been found in general that as increasing amounts of anti-glucose oxidase are added to a fixed amount of apoglucose oxidase, apoenzyme activation increases until a maximum activation is attained. The further addition or antiglucose oxidase does not result in further activation, and may actually lead to decreased activation. Excess anti-glucose oxidase accordingly will not be desirable. Titration of anti-glucose oxidase against glucose oxidase activity will indicate for a given amount of concentration of apoenzyme the optimum amount or concentration of anti-glucose oxidase to use.

The ability of anti-glucose oxidase to activate apoglucose oxidase occurs over a reasonably broad temperature range, running between 0° C. and temperatures at which the proteins denature significantly. The activation is particularly signficant over the range of 10° C. to 45° C., most particularly between about 30° C. and about 40° C.

The ability to activate apoglucose oxidase with anti-glucose oxidase provides particular advantages in application to FAD-labeled homogeneous specific binding assays. Such assays are basically characterized by the monitoring of the FAD label by its ability to combine with apoglucose oxidase to form active glucose oxidase. In accordance with the present invention, such apoglucose oxidase is activated by interaction with anti-glucose oxidase. The present invention is particularly applicable to an FAD-labeled homogeneous immunoassay method for determining a ligand in a liquid medium wherein a reaction mixture is formed by combining the liquid medium with reagent means including (a) a labeled conjugate comprising the FAD label coupled to said ligand or a binding analog thereof, i.e., a substance which is bound by the ligand binding partner substantially the same as the ligand, (b) an antibody to the ligand, and (c) apoglucose oxidase, and wherein glucose oxidase activity is thereafter measured in the reaction mixture as a direct function of the amount of ligand in the liquid medium under assay. Such assay method can be used to determine such ligands as antigenic proteins, including antibodies, and polypeptides having molecular weights between 1,000 and 10,000,000 and haptens having molecular weights between 100 and 1,500.

Alternatively, where the ligand under determination can bind with an FAD-labeled binding partner to the ligand to affect the ability of the FAD label to combine with apoglucose oxidase, such as where the ligand is a binding protein and the labeled binding partner is the substance bound thereby, the present invention is applicable to an FAD-labeled homogeneous immunoassay method for determining such a ligand in a liquid medium wherein a reaction mixture is formed by combining the liquid medium with reagent means including (a) a labeled conjugate comprising the FAD label coupled to said binding partner of the ligand and (b) apoglucose oxidase, and wherein glucose oxidase activity thereafter measured in the reaction mixture is an inverse function of the amount of ligand in the liquid medium under assay. Such ligand/binding partner pairs to which such a method is applicable include antibodies/hapten or antigen, thyroxine binding globulin/thyroxine or triiodothyronine, and the like.

When used in an FAD-labeled specific binding assay, apoglucose oxidase activation may be obtained by a variety of ways of interacting the apoenzyme with anti-glucose oxidase. In one embodiment, anti-glucose oxidase and the principal reagents of the assay, usually comprising (a) an FAD-labeled form of the ligand or an analog thereof, (b) a specific binding partner of the ligand, e.g., an antibody, (c) apoglucose oxidase, and (d) a glucose oxidase indicator system, are combined as separate reagents to form the assay reaction mixture. In another embodiment, some of the reagents are precombined, e.g., (a) apoglucose oxidase and the binding partner and (b) FAD-labeled conjugate and the glucose oxidase indicator system, and added to the others as combined reagents.

The anti-glucose oxidase and apoglucose oxidase may be added to the assay reaction mixture in the form of their activated complex. In cases of short assay incubation times and low analyte concentrations this may be preferable since in such a case essentially all of the apoglucose oxidase is in its activated form immediately upon formation of the assay reaction mixture. If added as separate reagents, the apoenzyme and anti-glucose oxidase require some finite time for complete activation of apoglucose oxidase by complexing with the anti-glucose oxidase. Where an apoglucose oxidase/anti-glucose oxidase complex reagent is used, it may be preferable to employ monovalent antibody fragments, e.g., Fab or F(ab'), as the anti-glucose oxidase. In this way one can prevent the possible formation of intermolecular crosslinks between apoglucose oxidase which otherwise could lead to the formation of suspensions or precipitates which could interfer with the assay reaction or the measured signal.

The reagent means of the present invention comprises all of the essential chemical elements required to conduct a desired assay method of the present invention. Such reagent means are presented in a commercially packaged form, as a composition or admixture where the compatibility of the reagents will allow, in a test device configuration of any present or future type, or as a test kit, i.e., a packaged combination of one or more containers or vessels holding the necessary reagents. The reagents of the present invention include (a) an FAD-labeled conjugate comprising FAD coupled to the ligand, a binding analog thereof, or a specific binding partner thereof, depending on the particular assay technique intended, (b) apoglucose oxidase, (c) where the FAD-labeled conjugate comprises the ligand or an analog thereof, a specific binding partner of the ligand (e.g., an antibody or other binding protein), and (d) anti-glucose oxidase as defined herein, and optionally one or more or all of an indicator composition for detecting glucose oxidase activity (e.g., comprising glucose, peroxidase and a chromogen or chromogen system responsive to hydrogen peroxide produced when glucose oxidase acts on glucose). Of course, the reagent means can include other substances as are known in the art and which may be desirable from a commercial and user standpoint, such as buffers, diluents, standards, and so forth.

The present invention will now be illustrated, but is not intended to be limited by the following examples.

Apoglucose oxidase substantially free from residual glucose oxidase activity is prepared by the method described in U.S. Pat. No. 4,268,631 assigned to the present assignee.

Theophylline-FAD conjugates are prepared by the method described in U.S. Pat. No. 4,238,565 assigned to the present assignee.

Sodium 3,5-dichloro-2-hydroxybenzene sulfonate (sodium DHSA) is prepared by hydrolysis of sodium 3,5-dichloro-2-hydroxybenzene sulfonyl chloride (Aldrich Chemical Co., Milwaukee, WI) with sodium bicarbonate solution.

Antibody to glucose oxidase is obtained by injecting goats on four subcutaneous sites near the shoulders with a total of 3.0 ml adjuvant (1.5 ml Freund's adjuvant and 1.5 ml saline) containing glucose oxidase in the range 0.1–1.0 mg. Complete Freund's adjuvant is used for the initial injection and incomplete Freund's adjuvant is used for the booster injections. Five weeks after the initial injection, the following schedule is followed at one week intervals: boost, bleed, bleed, rest, repeat.

EFFECT OF TEMPERATURE ON THE ACTIVATION OF APOGLUCOSE OXIDASE IN THE PRESENCE AND ABSENCE OF ANTISERUM AGAINST GLUCOSE OXIDASE

A. Reagents

Mix A—2 micromolar ($\mu$M) apoglucose oxidase in 0.1 molar (M) sodium phosphate buffer, pH 7.0, containing 4 millimolar (mM) aminophenazone, 10% glycerol, and 0.1% (w/v) bovine serum albumin. This mix was incubated at room temperature.

Mix B—1.0 nanomolar (nM) theophylline-FAD was added to a glucose oxidase assay reagent solution consisting of 0.1M sodium phosphate buffer, pH 7.0, 0.105M glucose, 2.11 mM sodium DHSA, 1.05% (w/v) bovine serum albumin and 63 micrograms per milliliter ($\mu$g/ml) peroxidase. Aliquots of this mix were incubated at the various temperatures indicated below.

B. Assays

Mix A [100 microliters ($\mu$l)] was mixed with either 10 $\mu$l of goat antiserum against glucose oxidase (anti-GO serum) or 10 $\mu$l of nonimmune goat serum (NI serum) in disposable cuvettes. The solutions were incubated at room temperature for 15 minutes. Mix B (1.90 ml) equilibrated to the desired assay temperature was then added and the reaction mixture mixed by inversion. After a 15 minute incubation at the desired assay temperature, the absorbance at 520 nanometers (nm) was read against Mix B. Blanks were also run exactly as above except that theophylline-FAD was absent from Mix B. The results are shown in tabular form below [and as a graph in FIG. 1 of the drawings]. The absorbance readings are corrected for the blank.

| Temperature | Absorbance (520 nm) | |
|---|---|---|
| (°C.) | NI serum | Anti-GO serum |
| 10 | 0.041 | 0.094 |
| 15 | 0.100 | 0.212 |
| 20 | 0.134 | 0.430 |
| 24 | 0.170 | 0.682 |
| 28 | 0.073 | 0.885 |
| 32 | 0.020 | 0.929 |
| 36 | NC* | 0.778 |
| 40 | NC* | 0.606 |

*no measurable color

These data demonstrate that the presence of anti-glucose oxidase antiserum enhances the ability of apoglucose oxidase to combine with the theophylline-FAD conjugate to form active glucose oxidase. At room temperature (25° C.), the presence of anti-glucose oxidase produces a 4-fold increase in apoglucose oxidase activation. The effect at 37° C. is estimated at between 100 and 1000-fold.

THEOPHYLLINE IMMUNOASSAY AT 37° C. IN THE PRESENCE AND ABSENCE OF ANTISERUM TO GLUCOSE OXIDASE

I. Assay in the absence of anti-glucose oxidase
Reagents:
Mix A—Combined apoenzyme/anti-theophylline reagent: 32 $\mu$M apoglucose oxidase and 50 $\mu$l anti-theophylline antiserum per ml were added to 0.1M sodium phosphate buffer, pH 7.0, containing 0.1% (w/v) bovine serum albumin. This mix was incubated at 20° C.

Mix B—Combined glucose oxidase assay and theophylline-FAD label: 63 nM theophylline-FAD was added to 0.1M sodium phosphate buffer, pH 7.01, containing 0.105M glucose, 2.11 mM sodium DHSA, 0.21 mM aminophenazone, 1.05% (w/v) bovine serum albumin, and 63 $\mu$g/ml horseradish peroxidase. This mix was incubated at 37° C.

Theophylline standards: Prepared by gravimetrically spiking pooled human serum with different amounts of theophylline. These standards were diluted 10-fold with 0.1M sodium phosphate buffer, pH 7.0.

Figure 2:
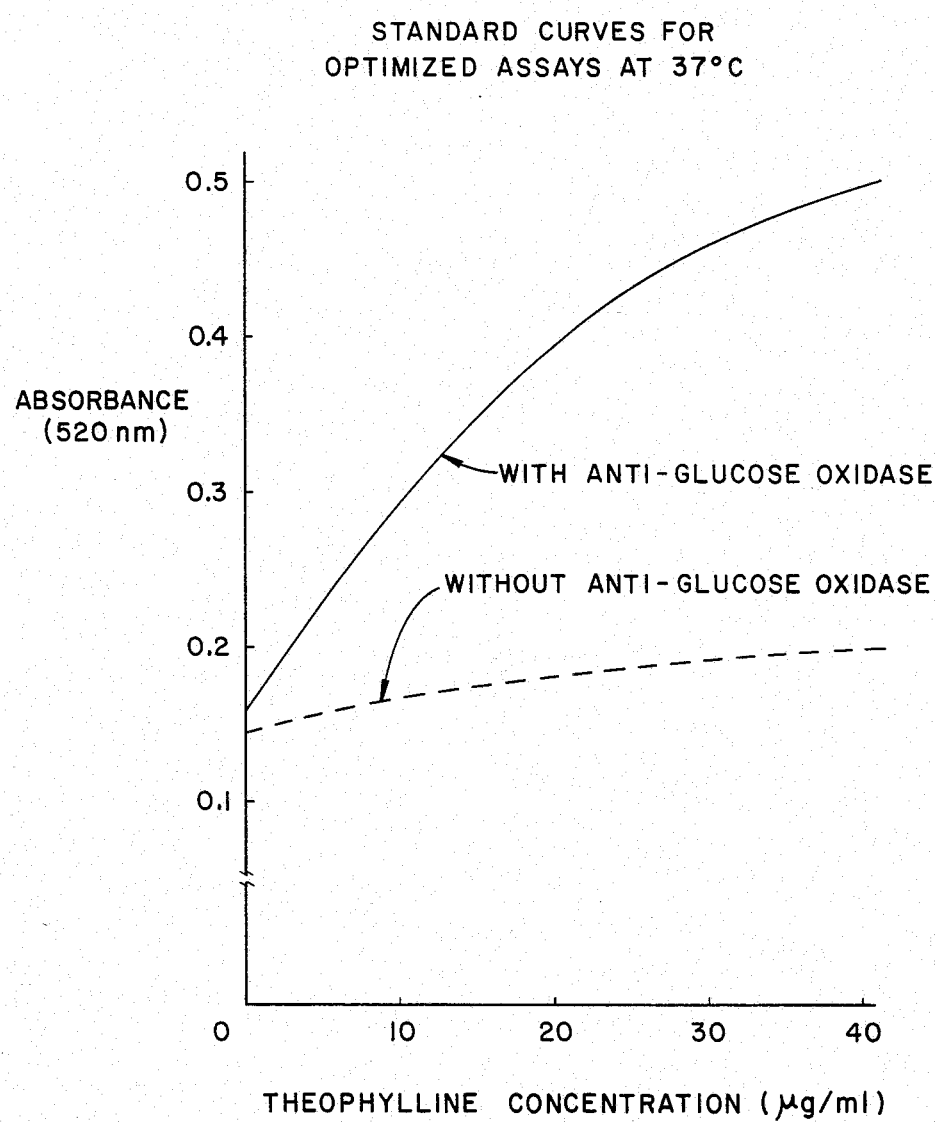
FIG. 2 is a graphical representation of data from the examples below showing optimized standard curves for a theophylline assay at 37° C. with and without anti-glucose oxidase.

Assay procedure: Mix B (1.90 ml) was mixed with 50 $\mu$l of a diluted theophylline standard in a disposable cuvette and equilibrated at 37° C. Mix A (0.10 ml) was then added and the reaction mixture mixed by inversion. After a 6 minute incubation at 37° C., the absorbance at 520 nm was read against Mix B. The final assay concentrations for the principal reagents were:

apoglucose oxidase—1.60 $\mu$M
theophylline-FAD—60 nM
anti-theophylline—2.5 $\mu$l/ml The results are shown in tabular form below and as a graph in FIG. 2 of the drawings.

| Theophylline serum concentration ($\mu$g/ml) | Absorbance (520 nm) |
|---|---|
| 0 | 0.146 |
| 6 | 0.162 |
| 12 | 0.174 |
| 20 | 0.183 |
| 30 | 0.190 |
| 40 | 0.198 |

The absorbance change over the full range of theophylline serum concentrations was only 0.052. This data represents the present optimized theophylline assay in the absence of anti-glucose oxidase.

II. Assay in the presence of anti-glucose oxidase
Reagents:
Mix A—600 nM apoglucose oxidase, 100 $\mu$l/ml rabbit antiserum against glucose oxidase, and 20 $\mu$l/ml anti-theophylline were added to 0.1M phosphate buffer, pH 7.0, containing 4 mM aminophenazone and 10% glycerol. This mix was incubated at room temperature.

Mix B—10.5 nM theophylline-FAD was added to 0.10M phosphate buffer, pH 7.0, 0.105M glucose, 2.11 mM sodium DHSA, 1.05% (w/v) bovine serum albumin, and 63 $\mu$g/ml horseradish peroxidase. This mix was incubated at 37° C.

Theophylline standards: Same as above.

Assay procedure: Mix B (1.90 ml) was mixed with 20 $\mu$l of a diluted theophylline standard in a disposable cuvette and equilibrated at 37° C. Mix A (0.10 ml) was then added and the reaction mixture mixed by inversion. After a 5 minute incubation at 37° C., the absorbance at 520 nm was read against Mix B. The final assay concentrations for the principal reagents were:

apoglucose oxidase—0.03 $\mu$M
theophylline-FAD—10 nM
anti-theophylline—1.0 $\mu$l/ml The results are shown in tabular form below and as a graph in FIG. 2 of the drawings.

| Theophylline serum concentration ($\mu$g/ml) | Absorbance (520 nm) |
|---|---|
| 0 | 0.162 |
| 10 | 0.298 |
| 20 | 0.378 |
| 30 | 0.444 |
| 40 | 0.495 |

The absorbance change over the full range of theophylline serum concentrations was 0.333 compared to 0.052 for the optimized assay without anti-glucose oxidase (part I above). Further, the theophylline assay at 37° C. with anti-glucose oxidase present required approximately 50-fold less apoglucose oxidase, 6-fold less theophylline-FAD conjugate, and 2.5-fold less anti-theophylline.

These data demonstrate the greatly improved features of the assay at 37° C. with antiglucose oxidase present over that without anti-glucose oxidase.

USE OF ANTIBODY FRAGMENTS TO ACTIVATE APOGLUCOSE OXIDASE

I. Preparation of anti-glucose oxidase IgG

Goat antiserum against glucose oxidase (35 ml) was dialysed against 2 liters of 15 mM potassium phosphate, pH 8.0, for 16 hours at room temperature. The dialysed solution was applied to a column (2.5×30 cm) DE-52 cellulose (Whatman Ltd., UK) equilibrated with 15 mM potassium phosphate, pH 8.0. The column was eluted with the same buffer at a flow rate of 50 ml/hour and 12 ml fractions were collected. The absorbance of the effluent was monitored at 280 nm. An initial absorbance peak was eluted in fractions 14 to 21 and this was pooled and labeled "FI". The eluting buffer was changed to 50 mM potassium phosphate, pH 8.0, and a second major absorbance peak was collected in fractions 39 to 44 which was pooled and labeled "FII". The two absorbance peaks correlated well with the ability of the fractions to activate apoglucose oxidase.

II. Papain digestion of anti-glucose-oxidase IgG (Fab fragments)

Protein from FI (50 mg) was incorporated into 5 ml of 50 mM sodium phosphate, pH 7.3, containing 0.15M sodium chloride, 25 mM cysteine, 1 mM ethylenediamine tetraacetic acid (EDTA) and 1 mg papain. The solution was incubated at 37° C. for 60 minutes.

Solid iodoacetamide (28 mg) was then added to give a 30 mM solution to quench the reaction. This solution was incubated for a further 15 minutes after which it was applied to a column (25×90 cm) of Sephadex G150 equilibrated with 50 mM sodium phosphate, pH 7.0, containing 0.02% (w/v) sodium azide. The column was developed by elution with the same buffer at a flow rate of 25 ml/hour and 4.6 ml fractions were collected. Absorbance at 280 nm was monitored and a peak eluted between fractions 47 to 72 was shown to contain a mixture of Fab and Fc fragments and correlated well with the ability of the fractions to activate apoglucose oxidase. This material was pooled, concentrated to 7.9 mg/ml protein and labeled "FI(a)". No whole IgG was eluted and it was concluded that complete digestion of IgG had occurred.

Protein from FII (50 mg) was digested as described above. Chromatography on Sephadex G150 was performed as described above. Absorbance peaks at 280 nm were eluted, one between fractions 34 to 50 which was identified as IgG and a second between fractions 56–75 which was shown to contain a mixture of Fab and Fc fragments. Both absorbance peaks correlated well with the ability of the fractions to activate apoglucose oxidase. The first peak was pooled, concentrated to 16.8 mg/ml and labeled "FII(a)". The second peak was pooled, concentrated to 6.2 mg/ml and labeled "FII(b)".

III. Activation of apoglucose oxidase by Fab fragments
 A. Reagents

Apoglucose oxidase (3.2 $\mu$M) was prepared in 0.1M sodium phosphate buffer, pH 7.0, containing 8 mM aminophenazone and 10% glycerol. The glucose oxidase assay reagent contained 0.10M sodium phosphate buffer, pH 7.0, 0.105M glucose, 2.11 mM sodium DHSA, 1.05% (w/v) bovine serum albumin, 63 $\mu$g/ml peroxidase, and 1.0 nM theophylline-FAD.

B. Assays

Aliquots (0.20 ml) of 0.10M sodium phosphate buffer, pH 7.0, containing antibody or antibody fragments were mixed with 0.03 ml of apoglucose oxidase reagent in a disposable cuvette and incubated at room temperature for 15 minutes. The glucose oxidase reagent (1.90 ml) was equilibrated at 37° C. and added to the cuvette. The assay solution was incubated at 37° C. for 15 minutes and the absorbance read at 520 nm against the glucose oxidase reagent solution as reference. The recorded absorbances were corrected for a blank (assay solution without theophylline-FAD).

The results were as follows:

| Protein ($\mu$g) | Absorbance (520 nm) |
|---|---|
| Activation by FI(a) - Fab and Fc fragments | |
| 0 | 0.050 |
| 80 | 0.300 |
| 160 | 0.555 |
| 320 | 0.700 |
| 400 | 0.900 |
| 800 | 0.922 |
| 1600 | 0.778 |
| Activation by FII(a) - whole IgG | |
| 0 | 0.050 |
| 84 | 0.405 |
| 168 | 0.779 |
| 252 | 0.910 |
| 420 | 1.044 |
| 840 | 1.094 |
| 1680 | 1.140 |
| Activation by FII(b) - Fab and Fc fragments | |
| 0 | 0.050 |
| 62 | 0.257 |
| 124 | 0.504 |
| 186 | 0.693 |
| 310 | 0.918 |
| 620 | 1.046 |
| 1240 | 1.000 |

These data demonstrate that fragments (Fab) of antiglucose oxidase antibody are effective in activating apoglucose oxidase.

ACTIVATION OF APOGLUCOSE OXIDASE BY ANTISERUM ADSORBED WITH DENATURED APOGLUCOSE OXIDASE

Apoglucose oxidase was heat denatured by incubating a 25 $\mu$M solution of apoenzyme in 0.1M phosphate buffer, pH 7.0 at 37° C. for 60 minutes until no detectable apoenzyme activity remained. Active apoenzyme solution consisted of 1 $\mu$M apoglucose oxidase in 0.1M phosphate buffer, pH 7.0, containing 30% (w/v) glycerol, 8 mM aminoantipyrine and 0.1% (w/v) sodium azide. Label solution consisted of 5 nM theophylline-FAD conjugate. 2.1 mM, 3,5-dichloro-2-hydroxybenzene sulfonate, 1.05M glucose, 60 $\mu$g/ml peroxidase and 0.1M phosphate, pH 7.0:

Antiglucose oxidase serum was adsorbed by mixing 1.0 ml of serum with 0.4 ml of heat denatured apoenzyme (10 nmoles) and 0.6 ml 0.1M phosphate buffer, pH 7.0. A control antiglucose oxidase serum solution was prepared by diluting the serum two fold with phosphate buffer. Assays were performed by mixing active apoenzyme solution, antiserum solution and buffer in the compositions shown in Table A. The solutions were incubated at room temperature for 5 minutes and the reaction started by addition of 2.9 ml label solution equilibrated to 37° C. The assay was incubated for 10 minutes at 37° C. and the absorbance at 520 nm recorded. The average absorbance of duplicates is shown in Table A.

TABLE A

| Active apoenzyme solution ($\mu$l) | Control antiserum ($\mu$l) | Adsorbed antiserum ($\mu$l) | Buffer ($\mu$l) | Absorbance at 520 nm |
|---|---|---|---|---|
| 50 | 0 | — | 100 | 0 |
| 50 | 5 | — | 95 | 1.129 |
| 50 | 10 | — | 90 | 1.148 |
| 50 | 20 | — | 80 | 1.027 |
| 50 | 60 | — | 40 | 0.459 |
| 50 | 100 | — | 0 | 0.187 |
| 50 | — | 5 | 95 | 1.049 |
| 50 | — | 10 | 90 | 1.159 |
| 50 | — | 20 | 80 | 1.225 |
| 50 | — | 60 | 40 | 1.208 |
| 50 | — | 100 | 0 | 1.214 |

THE PERFORMANCE OF IMMUNOASSAY REAGENT STRIPS AT 37° C. IN THE PRESENCE AND ABSENCE OF ANTI-GLUCOSE OXIDASE

Reagent strip for determining theophylline were prepared as follows: Three (3) sets of Whatman 31 ET paper (Whatman Inc., Clifton, NJ, USA) were impregnated with a solution comprising:

0.36M phosphate-citrate buffer, pH 6.1
19 U/ml peroxidase
12 $\mu$l/ml anti-theophylline antiserum
3 $\mu$M FAD binding sites of apoglucose oxidase
0.1M glucose
0, 10, or 50 $\mu$l antiglucose oxidase (anti-GO) per nmole apoenzyme FAD binding sites for sets 1, 2, and 3, respectively Following impregnation, the paper was dried in a forced air oven at 50° C. for 4.5 minutes. The dried paper was impregnated with a second solution comprising:

5 mM 3,3',5,5'-tetramethylbenzidine
2% (w/v) Gantrez ES-225 (GAF Corp., N.Y., NY, USA)
0.3% (w/v) Aerosol OT (dioctosodium sulfosuccinate), Aldrich Chemical Co., Milwaukee, WI, USA).
0.4 $\mu$M FAD-theophylline conjugate in acetone Following this second impregnation, the paper was again dried in a forced air oven at 50° C. for 4.5 minutes. The impregnated paper was used to make test strips each having a 0.2×0.4 inch pad of the reagent-laden paper mounted ¼ inch from the end of biaxially oriented polystyrene strip measuring about 0.5 by 8.3 cm. Mounting was achieved using a double-faced adhesive tape known as Double-Stick (3M Company, Minneapolis, MN, USA).

These strips were tested for their responsiveness to various concentrations of theophylline by pipetting 30 $\mu$l of the test solution onto the reagent pad and analyzing the strips using the SERALYZER ® Reflectance Photometer (Ames Division, Miles Laboratories, Inc., Elkhart, IN, USA). The reflectance data obtained at 740 nm at a fixed time of 90 seconds is converted to K/S values which is defined as follows:

$$K/S = \frac{(1 - R)^2}{2R}$$

in which K is a constant, S is the scattering coefficient of the particular reflecting medium, and R is the fraction of reflectance from the test strip. This relationship is a simplified form of the Kubelka-Munk equation (Gustav Kortum, "Reflectance Spectroscopy", pp. 106–111. Springer-Verlag, NY (1969).

The dose response data for strip sets 1, 2 and 3 are presented below:

| Theophylline ($\mu$g/ml) | K/S values (Anti-GO amount) | | |
|---|---|---|---|
| | Set 1 (0 $\mu$l) | Set 2 (10 $\mu$l) | Set 3 (50 $\mu$l) |
| 0 | 0.1080 | 0.2180 | 0.3485 |
| 0.2 | 0.1078 | 0.2771 | 0.5967 |
| 0.6 | 0.1131 | 0.3920 | 1.304 |
| 1.0 | 0.1091 | 0.5208 | 2.031 |
| 1.2 | 0.1106 | 0.5737 | 2.203 |
| 1.6 | 0.1091 | 0.7011 | 2.839 |

The data show that in the absence of anti-glucose oxidase the strips (set 1) showed essentially no response to theophylline, whereas, where antibody was present (sets 2 and 3) a quite useful response was obtained.

What is claimed is:

1. A method for increasing the ability of apoglucose oxidase to combine with flavin adenine dinucleotide and derivatives thereof to form active glucose oxidase comprising the step of interacting apoglucose oxidase with anti-glucose oxidase.

2. The method of claim 1 wherein said anti-glucose oxidase comprises an antibody, or a fragment thereof, to glucose oxidase.

3. The method of claim 2 wherein said antibody is of the IgG class.

4. The method of claim 3 wherein said anti-glucose oxidase comprises an Fab, F(ab'), or F(ab')$_2$ fragment of said antibody.

5. In a homogeneous specific binding assay method for determining a ligand in a liquid medium comprising the steps of:

forming a reaction mixture by contacting said liquid medium with
  (a) reagent means including a labeled conjugate comprising, as label component, flavin adenine dinucleotide coupled to a binding component, such contact producing a binding reaction system in which a bound-species and a free-species of said labeled conjugate are formed, the proportion of the flavin adenine dinucleotide label component in said two formed species being a function of the presence of said ligand in said liquid medium, and
  (b) apoglucose oxidase, the ability of the flavin adenine dinucleotide label component to combine with the apoglucose oxidase to produce the holoenzyme glucose oxidase being different in activity in said two formed species, and
determining the proportion of the flavin adenine dinucleotide label component in said two formed species by measuring glucose oxidase activity in said reaction mixture;

the improvement which comprises immunologically binding said apoglucose oxidase with anti-glucose oxidase prior to the measurement of glucose oxidase activity in the reaction mixture, whereby the apoglucose oxidase is activated to recombination with the flavin adenine dinucleotide label.

6. The method of claim 5 wherein said anti-glucose oxidase comprises an antibody, or a fragment thereof, to glucose oxidase.

7. The method of claim 6 wherein said antibody is of the IgG class.

8. The method of claim 7 wherein said anti-glucose oxidase comprises an Fab, F(ab'), or F(ab')$_2$ fragment of said antibody.

9. In a homogeneous specific binding assay method for determining a ligand in a liquid medium, comprising the steps of:

forming a reaction mixture by combining said liquid medium with reagent means including (1) a labeled conjugate comprising, as label component, flavin adenine dinucleotide coupled to said ligand or a binding analog thereof, (2) a specific binding partner of said ligand, and (3) apoglucose oxidase, wherein the binding by said binding partner of said ligand or analog thereof in said labeled conjugate inhibits the ability of the flavin adenine dinucleotide label component to combine with the apoglucose oxidase to produce the holoenzyme glucose oxidase; and measuring the resulting glucose oxidase activity in said reaction mixture;

the improvement which comprises immunologically binding said apoglucose oxidase with anti-glucose oxidase prior to the measurement of glucose oxidase activity in the reaction mixture, whereby the apoglucose oxidase is activated to recombination with the flavin adenine dinucleotide label.

10. The method of claim 9 wherein said anti-glucose oxidase comprises an antibody, or a fragment thereof, to glucose oxidase.

11. The method of claim 10 wherein said antibody is of the IgG class.

12. The method of claim 19 wherein said antiglucose oxidase comprises as Fab, F(ab'), or F(ab')$_2$ fragment of said antibody.

13. The method of any one of claims 9 or 10-12 wherein said anti-glucose oxidase is added to said reaction mixture in the form of its binding complex with said apoglucose oxidase.

14. The method of claim 13 wherein said reaction mixture is maintained at a temperature between about 30° C. and about 40° C.

15. The method of claim 14 wherein said temperature is maintained at about 37° C.

16. In reagent means for determining a ligand in a liquid medium by a homogeneous specific binding assay method, which means includes (a) a labeled conjugate having, as a label component, flavin adenine dinucleotide coupled to a binding component, and (b) apoglucose oxidase, wherein the ability of the flavin adenine dinucleotide label component to combine with the apoglucose oxidase to produce the holoenzyme glucose oxidase is different when the binding component in said conjugate is bound by a specific binding counterpart thereto compared to when such component is not so bound, the improvement which comprises anti-glucose oxidase.

17. The reagent means of claim 16 wherein said anti-glucose oxidase comprises an antibody, or a fragment thereof, to glucose oxidase.

18. The reagent means of claim 17 wherein said antibody is of the IgG class.

19. The reagent means of claim 18 wherein said anti-glucose oxidase comprises an Fab, F(ab'), or F(ab')$_2$ fragment of said antibody.

20. The reagent means of any one of claims 16 or 17-19 wherein said anti-glucose oxidase is present in the form of its binding complex with said apoglucose oxidase.

21. A test kit for determining a ligand in a liquid medium, comprising
(1) a labeled conjugate comprising, as label, flavin adenine dinucleotide coupled to said ligand or a binding analog thereof,
(2) a specific binding partner of said ligand,
(3) apoglucose oxidase, and
(4) anti-glucose oxidase, wherein said conjugate, binding partner, apoglucose oxidase, and anti-glucose oxidase are present in amounts capable of determining said ligand in a liquid medium.

22. The test kit of claim 21 wherein said anti-glucose oxidase comprises an antibody, or a fragment thereof, to glucose oxidase.

23. The test kit of claim 22 wherein said antibody is of the IgG class.

24. The test kit of claim 23 wherein said anti-glucose oxidase comprises an Fab, F(ab'), or F(ab')$_2$ fragment of said antibody.

25. The test kit of any one of claims 21-24 wherein said anti-glucose oxidase is present in the form of its binding complex with said apoglucose oxidase.

26. The test kit of claim 21 wherein said specific binding partner of said ligand is an antibody to said ligand.

27. The test kit of claim 26 wherein said ligand is a hapten.

28. A test kit for determining a ligand in a liquid medium, comprising
(1) a labeled conjugate comprising, as label, flavin adenine dinucleotide coupled to a specific binding partner of said ligand,
(2) apoglucose oxidase, and
(3) anti-glucose oxidase,
wherein said conjugate, apoglucose oxidase, and anti-glucose oxidase are present in amounts capable of determining said ligand in a liquid medium.

29. The test kit of claim 28 wherein said anti-glucose oxidase comprises an antibody, or a fragment thereof, to glucose oxidase.

30. The test kit of claim 29 wherein said antibody is of the IgG class.

31. The test kit of claim 30 wherein said anti-glucose oxidase comprises an Fab, F(ab'), or F(ab')$_2$ fragment of said antibody.

32. The test kit of any one of claims 28-31 wherein said anti-glucose oxidase is present in the form of its binding complex with said apoglucose oxidase.

33. The test kit of claim 28 wherein said ligand is an antibody and said binding partner is a hapten or antigen bound thereby.

* * * * *